United States Patent [19]

Levy et al.

[11] Patent Number: 4,722,730

[45] Date of Patent: Feb. 2, 1988

[54] APPARATUS FOR RELIEF OF FETAL DISTRESS DURING LABOR

[75] Inventors: Jeffrey Levy, Cicero; Bruce Rosenzweig, Wilmette, both of Ill.

[73] Assignee: Michael Reese Hospital and Med. Center, Chicago, Ill.

[21] Appl. No.: 833,979

[22] Filed: Feb. 27, 1986

[51] Int. Cl.$^4$ .................... A61M 1/00; A61B 5/10
[52] U.S. Cl. .................... 604/118; 128/748; 128/775; 128/778
[58] Field of Search ............ 604/55, 264, 280, 118; 128/748, 772, 775, 778, 654, 747

[56] References Cited

U.S. PATENT DOCUMENTS

| | | | |
|---|---|---|---|
| 2,480,041 | 8/1949 | Myller | 128/654 |
| 2,845,930 | 8/1958 | Brown | 604/118 |
| 3,094,124 | 6/1963 | Birtwell | 604/280 |
| 4,136,681 | 1/1979 | Hon | 128/748 |
| 4,168,703 | 9/1979 | Kenigsberg | 128/748 |
| 4,252,131 | 2/1981 | Hon et al. | 128/748 |
| 4,325,387 | 4/1982 | Helfer | 128/778 |
| 4,405,313 | 9/1983 | Sisley et al. | 604/264 |
| 4,456,013 | 6/1984 | De Rossi et al. | 128/748 |
| 4,476,871 | 10/1984 | Hon | 128/778 |
| 4,543,965 | 10/1985 | Pack et al. | 128/748 |
| 4,548,205 | 10/1985 | Armeniades et al. | 128/748 |

OTHER PUBLICATIONS

Miyazaki et al., Amer. J. Obstet. Gynecol., 146, pp. 670–678, 1983.
Miyazaki et al., Amer. J. Obstet. Gynecol., 153, pp. 301–306, 1985.
Gabbe et al., Amer. J. Obstet. Gynecol., 126, pp. 353–355, 1976.
Nageotte et al., Amer. J. Obstet. Gynecol., 153, pp. 557–562, 1985.

*Primary Examiner*—C. Fred Rosenbaum
*Assistant Examiner*—Gene B. Kartchner
*Attorney, Agent, or Firm*—Dressler, Goldsmith, Shore, Sutker & Milnamow, Ltd.

[57] ABSTRACT

The present invention relates to an apparatus for simultaneously monitoring intrauterine pressure and delivering infusible fluids therein for relief of fetal distress during labor with ruptured membranes. The apparatus comprises a catheter assembly having a first and second catheter and a guide tube for providing passage of the catheter assembly therethrough into the uterus.

10 Claims, 5 Drawing Figures

U.S. Patent   Feb. 2, 1988   4,722,730
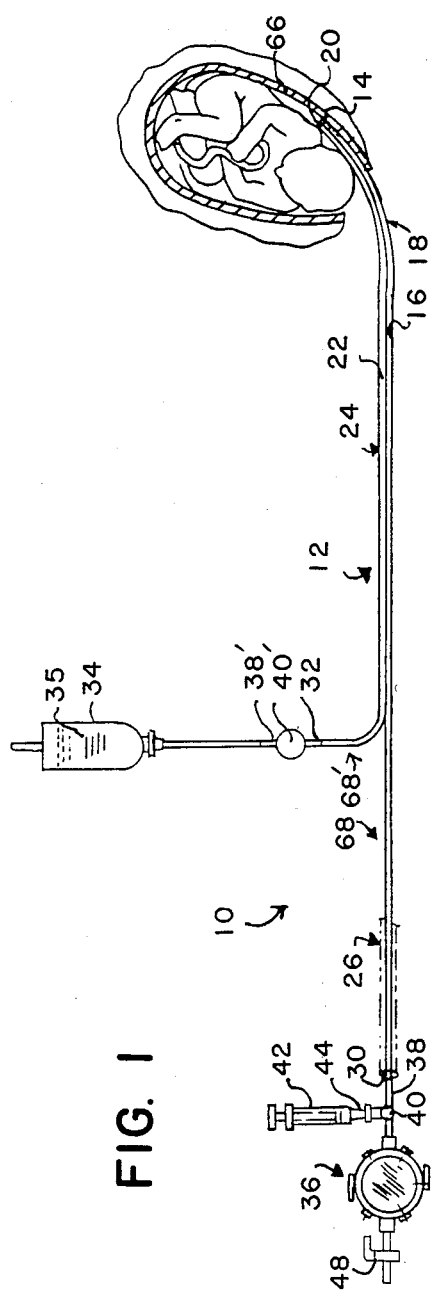
FIG. 1
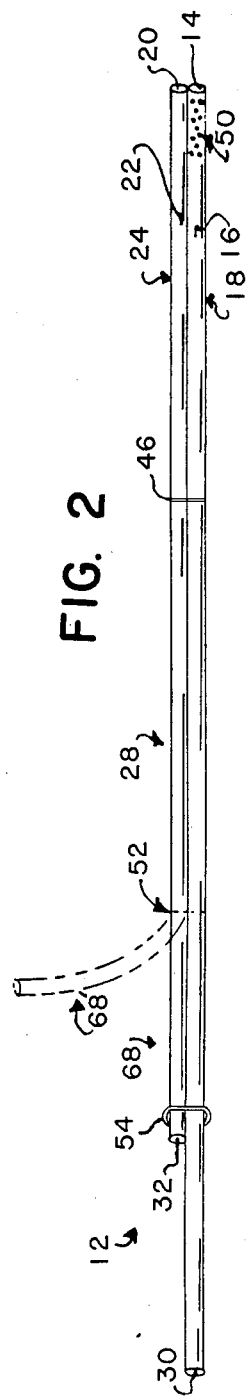
FIG. 2
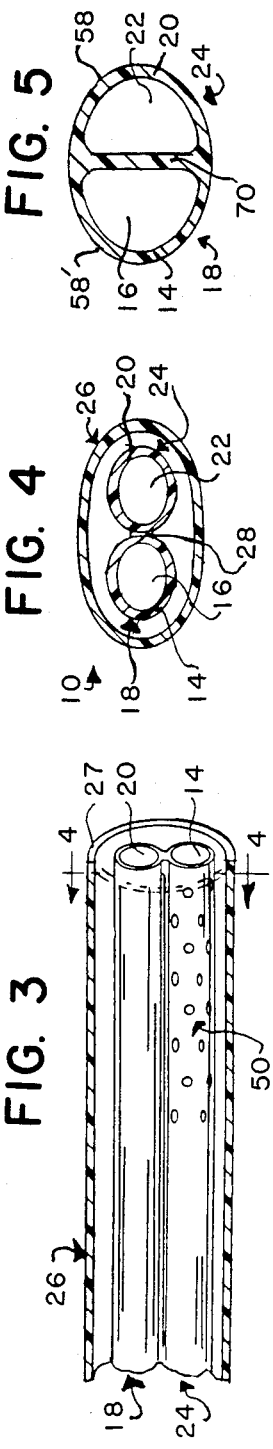
FIG. 3
FIG. 4
FIG. 5

APPARATUS FOR RELIEF OF FETAL DISTRESS DURING LABOR

TECHNICAL FIELD

The present invention relates to an apparatus for simultaneously monitoring intrauterine pressure and delivering infusible fluids therein for relief of fetal distress during labor. More particularly, this invention relates to an apparatus comprising a catheter assembly having a first and second catheter and a guide tube for introduction into a body cavity.

BACKGROUND OF THE INVENTION

During labor, it is sometimes necessary to monitor intrauterine pressure to more accurately assess contractions, and to aid in the detection of fetal distress so that appropriate remedial action can be taken. A condition that is frequently associated with fetal distress during labor is variable decelerations owing to a state of oligohydramnios, i.e., the presence of less than 300 milliliters amniotic fluid at term.

Loss of amniotic fluid is particularly of serious concern when it brings on a state of oligohydramnios during the intrapartum period of advanced labor with ruptured membranes. Amniotic fluid provides constant lubrication between the fetus, umbilical cord, and membranes. It also protects the fetus from external trauma and pressure by equalizing forces applied to the intrauterine contents.

Consequently, without adequate intrauterine fluid volume, fetal distress may occur. This distress may result from umbilical cord occlusion by entrapment between the fetus and the uterine wall, entanglement about the fetus, or from placental compression.

It is desirable, therefore, to maintain an adequate amniotic fluid volume in order to prevent these complications. Remedial action by intrauterine saline amnioinfusion therapy has been found useful for relieving fetal distress by replenishing intrauterine fluid volume to overcome the effects of oligohydramnios.

A discussion of amnioinfusion therapy can be found in Miyazaki et al., *Amer. J. Obstet. Gynecol.*, 146, pages 670–678, 1983, (hereafter Miyazaki I); in Miyazaki et al., *Amer. J. Obstet. Gynecol.*, 153, pages 301–306, 1985 (hereafter Miyazaki II); and in Gabbe et al., *Amer. J. Obstet. Gynecol.*, 126, pages 353–355, 1976; and in Nageotte et al., *Amer. J. Obstet. Gynecol.*, 153, pages 557–562, 1985.

A fluid filled intrauterine pressure catheter is typically used to effectively measure uterine contractions to avoid introducing air into the uterus and to measure the force of the intrauterine contractions transmitted through the uterine fluids and the liquid in the catheter to a pressure-measuring device, such as a strain gauge, a transducer, or the like.

In practicing amnioinfusion therapy, however, there is a need to simultaneously infuse fluids into the uterus and constantly monitor intrauterine pressure. As will be appreciated, this need particularly arises under emergency conditions, such as sudden severe prolonged decelerations.

In the past, attempts were made in Miyazaki I to infuse saline into the uterus by means of the fluid-filled pressure catheter by placing an extension tube leading to the saline in the line intermediate the transducer and the intrauterine catheter. However, this setup resulted in artificial pressure readings owing to resistance to outflow of the saline through the tip of the catheter, and a true reading could only be taken by shutting off the infusion flow.

As can be appreciated, under emergency conditions of sudden severe prolonged decelerations, it is necessary to rapidly infuse the uterus. Prior attempts with the setup described in Miyazaki II required connecting the intrauterine saline delivery tubing directly to the intrauterine pressure catheter, thereby foregoing the monitoring of the pressure altogether during saline delivery. Such a disability is a serious one, because the period of saline delivery is a period of flux, and it is especially necessary to monitor pressure during a period of flux.

There is a need, therefore, for an apparatus that allows for simultaneously monitoring intrauterine pressure during labor and delivering infusible fluid therein. To resolve the difficulty noted above, this invention relates to an apparatus that achieves the foregoing purpose.

SUMMARY OF THE INVENTION

In accordance with the present invention, an apparatus is disclosed that provides for simultaneously monitoring intrauterine pressure in the body during labor and delivering infusible fluids therein to relieve fetal distress. Generally, the apparatus comprises a flexible catheter assembly comprised of a first and second catheter and a flexible guide tube providing for passage of the catheter assembly through the vaginal and cervical canal into the uterus. Also disclosed herein is a method for practicing amnioinfusion therapy for relieving fetal distress with an apparatus of this invention.

In an embodiment of the present invention, the catheter assembly is comprised of a first catheter defining a first lumen being in fluid communication with a first body end opening and a first distal end opening adapted for connection to a transducer or like pressure monitoring device, and a second catheter defining a second lumen being in fluid communication with a second body end opening and a second distal end opening adapted for connection to an infusion bag containing an infusible fluid.

The respective lumens of the first and second catheters are preferably substantially circular in circumference. The first and second catheters are preferably substantially coterminous at their respective body end openings, being in substantially contiguous spaced relationship with their respective lumens parallel and in close proximity to each other along a substantially major portion of their respective paths intermediate their respective body end opening and the distal end opening. The lumens are further readily separable to be non-contiguous in their respective paths beyond the contiguous portion of the catheter assembly.

In accordance with one aspect of the invention, the guide tube is open at both ends with a rearward opening for ingress of the catheter assembly and a rounded forward end opening for egress of the catheter assembly. The guide tube is configured to define a path within the body cavity of the vaginal and cervical canal of a human. The guide tube is also preferably substantially circular in circumference and sized to receive the catheter assembly and permit passage of the coterminous body end opening of the first and second catheters via the vaginal and cervical canal into the uterus.

The catheter assembly is longer and more flexible than the guide tube, and the guide tube has an inner diameter large enough to permit passage of the catheter assembly therethrough with substantially no friction. The guide tube is further configured to slide rearwardly along the catheter assembly for removal from the vaginal canal once the catheter assembly is appropriately positioned.

In a preferred embodiment, the first body end opening of the first catheter has a plurality of perforations along an external wall portion of the tip of said catheter positioned in the uterus. In actual practice, as described hereinbelow, the first and second catheter, prior to introducing them in utero, are flushed with fluid, such as sterile water, retaining fluid therein to minimize the likelihood of introducing air into the uterus. Additionally, the first catheter is sometimes flushed to clean it of intrauterine matter during amnioinfusion therapy. Towards this end, therefore, provision is further made for including a syringe means having its leading edge in fluid connection intermediate the first distal end of the first catheter and the transducer, and an adapter therefor.

In carrying out the invention, the catheter assembly is further provided by an indicia intermediate the respective body end openings and distal end openings and located along the substantially contiguous portions of the respective paths of the first and second catheter for sounding the depth of positioning in the uterus.

In one form of the present invention, the respective lumens of the first and second catheters of the catheter assembly are bonded in substantially contiguously spaced relationship along a parallel portion of their respective paths rearwardly of the coterminous body end openings and the second distal end opening of the second catheter. In manufacturing the apparatus of this invention, the lumens of the first and second catheter can be bonded as by a membrane, adhesive, molding sprue, or the like. The contiguous portion of the catheter assembly should be desirably bonded so as not to be readily separable at or near the respective body end openings of the first and second catheter rearwardly of the coterminous body end openings and the indicia. The lumens can be bonded with a weakening point along said bonding intermediate the indicia and their respective first and second distal end openings so as to be separable and non-contiguous in their respective paths. In another aspect of the present invention, the respective lumens of the first and second catheters of the catheter assembly are divided from each other by a common internal wall along the contiguous spaced parallel portion of their respective paths.

One benefit of the present invention is that intrauterine pressure can be continuously monitored simultaneously with the delivery of infusible fluids therein during the practice of amnioinfusion therapy.

Another benefit is that the catheter assembly, the guide tube, and their associated adapter fitments can be made of disposable materials and packaged in sterile condition for one-time use, thereby eliminating costly cleaning and lessening the chance of infection.

Numerous other advantages and features of the present invention will become readily apparent from the following detailed description, the accompanying drawings, and the appended claims.

BRIEF DESCRIPTION OF THE DRAWINGS

FIG. 1 is a schematic illustration of the apparatus of this invention in operative use for amnioinfusion therapy.

FIG. 2 is a lengthwise view of the catheter assembly portion of the apparatus shown in FIG. 1.

FIG. 3 is an enlarged lengthwise sectional perspective view of the coterminous body end opening of the first and second catheter of the catheter assembly shown in FIG. 2 received in the guide tube.

FIG. 4 is an enlarged cross-sectional view of the coterminous body end openings of the first and second catheter of the catheter assembly received in the guide tube taken substantially along the line 4—4 of FIG. 3.

FIG. 5 is an enlarged cross-sectional view similar to FIG. 4, but illustrating a further embodiment of the coterminous body end openings of the first and second catheter of the catheter assembly.

DETAILED DESCRIPTION OF THE INVENTION

While this invention is susceptible of embodiment in many different forms, there is shown in the drawings, and will herein be described in detail, a specific embodiment, with the understanding that the present disclosure is to be considered as an exemplification of the principles of the invention and is not intended to limit the invention to the embodiment illustrated.

Referring first to FIG. 1, therein is illustrated the apparatus 10 embodying the principles of this invention in operation for practicing amnioinfusion therapy for the intrauterine relief of fetal distress in the body during labor. In this illustrated embodiment, the apparatus 10 is shown with the catheter assembly 12 positioned so that the first body end opening 14 of the first lumen 16 of the first catheter 18 and the second body end opening 20 of the second lumen 22 of the second catheter 24 are in the uterus 66.

In this illustration, the catheter assembly 12 has already been advanced through the guide tube 26 (not shown) through the vaginal and cervical canal (not shown), sounding the placement in the uterus by an indicia 46 (not shown) intermediate their respective body end openings 14 and 20 and their non-contiguous respective paths 68 and 68'. The first catheter 18 and the second catheter 24 of the catheter assembly 12 are shown in substantially contiguously spaced relationship 28 with their respective lumens 16 and 22 parallel and in close proximity to each other along a major portion of their respective paths rearward of their respective body end openings 14 and 20.

The guide tube 26 being removed from the body cavity following introduction of the catheter assembly 12 is adapted to slide rearwardly along the length of the catheter assembly 12 to a point beyond the contiguous portion 28 of the first catheter 18 and second catheter 24. Thus, the guide tube 26 can be positioned, shown in phantom line, near the first distal end opening 30 of the first catheter 18 so as not to obstruct the connection of the second distal end opening 32 of the second catheter 24 to the infusion bag 34 containing infusible fluid 35, such as normal saline, or like physiologically compatible fluid.

Alternatively, the guide tube 26 can be removed completely from the catheter assembly 12 prior to connecting the first distal end opening 30 of the first catheter 18 with a transducer 36 or like pressure monitoring device. Preferably, the guide tube 26 can be scored laterally along at least one lateral side to provide a weakening point to break away under relatively mild pressure, such as squeezing or twisting, for easy removal and disposal.

In the illustrated embodiment of FIG. 1, the first catheter 18 is further provided with a first adapter 38, such as a needle-nose type adapter, for connection to a first fluid control valve means 40 intermediate the connection of the first distal end opening 30 and the transducer 36. For purposes of flushing the first catheter with a sterile fluid, such as water, a syringe 42 is provided with its leading edge 44 in fluid connection with the first fluid control valve means 40.

The first and second catheter 18 and 24 are preferably flushed with sterile fluid, such as water, prior to inserting the catheter assembly 12 into the uterus to minimize introducing air into the uterus and to provide for transmitting the force of the intrauterine contractions through the fluid remaining in the first catheter 18 to the transducer 36. The syringe 42 can also be used to flush the first catheter 18 in the event the perforated first body end opening 14 of the first catheter 18 accumulates intrauterine fluids during contractions. When the first catheter 18 is being so flushed or filled, the transducer 36 is vented, and for that purpose, a venting control valve means 48 is further provided.

Turning now to FIG. 2, a lengthwise view of the catheter assembly 12 portion of the apparatus 10 shown on FIG. 1 is illustrated. As best shown in FIG. 2, the catheter assembly 12 is comprised of a first catheter 18 defining a first lumen 16 being in fluid communication with a first body end opening 14 and a first distal end opening 30 and a second catheter 24 defining a second lumen 22 being in fluid communication with a second body end opening 20 and a second distal end opening 32. In a preferred embodiment illustrated in FIG. 2, the distal end opening of the first catheter 30 is substantially longer than that of the distal end opening of the second catheter 32.

The body end opening 14 of the first catheter 18 is further provided with a plurality of perforations 50 (one indicated) along the external wall of the tip portion of the first body end opening 14. The perforations 50 are in fluid communication with the first lumen 16 of the first catheter 18, and are sufficient in number to permit the measure of intrauterine fluid pressure transmitted therethrough. Preferably, these perforations are located along a portion of the tip of the first catheter 18 of about 3 to about 7 centimeters, more preferably about 5 centimeters. The respective lumens 16 and 22 of the first catheter 18 and the second catheter 24 are substantially circular in circumference, and the first catheter 18 and second catheter 24 are substantially coterminous at their respective body end openings 14 and 20.

The catheter assembly 12 is preferably manufactured and packaged so that the first catheter 18 and second catheter 24 are with their respective lumens 16 and 22 parallel and in close proximity to each other along a substantially major portion of their respective paths rearwardly of their respective body end openings 14 and 20 and the distal end openings 30 and 32. The catheter assembly 12 is further provided by an indicia 46 intermediate the body end openings 14 and 20 and the distal end openings 30 and 32 of the substantially parallel portions of the respective paths of the first catheter 18 and second catheter 24 for sounding the depth of their respective body end openings 14 and 20 in the uterus. The indicia 46 is preferably positioned at a point sufficient to mark a distance from the vaginal introitus (not shown) to the coterminous body end openings 14 and 20 of the catheter assembly 12 when it is introduced into the uterus (not shown). A useful distance for positioning the indicia 46 is at about 18 to about 25 percent, preferably at about 20 to about 22 percent of the length of the first cathether 18, rearwardly of the first body end opening 14. The indicia can be a permanent marking, such as an indelible black marking or any like readily visible marker.

In the embodiment illustrated in FIG. 2, the respective lumens 16 and 22 of the first and second catheter 18 and 24 are bonded in substantially contiguous spaced relationship 28 along a parallel portion of their respective paths rearwardly of their coterminous body end openings 14 and 20 and the second distal end opening 32 of the second catheter 24. The respective lumens 16 and 22 of the first and second catheter 18 and 24 are preferably in contiguous spaced relationship so as not to be readily separable at or near the body end openings 14 and 20 rearwardly of the coterminous body end openings and the indicia 46. More preferably, the respective lumens 16 and 22 of the first and second catheters 18 and 24 are in contiguous spaced relationship rearwardly of the indicia 46 to a location 52 beyond which the lumens 16 and 22 of the first and second catheters 18 and 24 are non-contiguous 68 and 68' (shown in phantom line) and are readily separable at their respective distal end openings 30 and 32. For this purpose, the catheter assembly 12 can be provided with a readily disposable securing member 54 at or near the second distal end opening 32 of the second catheter 24 that can be readily removed and disposed of when the catheter assembly 12 is ready for use.

In a particularly preferred embodiment of the type illustrated in FIG. 2, the first and second catheters 18 and 24 are in substantially contiguous spaced relationship along a major portion of their respective lengths representing about 40 to about 50 percent of the length of the catheter assembly 12 rearwardly of the first body end opening 14 of the first catheter 18, and the non-contiguous portion 52 of the catheter assembly 12. The non-contiguous portion represents about 20 to about 25 percent of the length of the second catheter 24 forwardly from the distal end opening 32. It will be appreciated that the portions of contiguous and non-contiguous lengths of the catheter assembly 12 can be determined on the basis of convenience and safety.

In one embodiment that is particularly preferred, the path of the first lumen 16 of the first catheter 18 is about 1.5 to about 1.75 times longer than the path of the second lumen 22 of the second catheter 24, with a contiguous portion representing a path of about 75 to about 85 percent rearwardly of the respective coterminous body end openings of the first and second catheter 18 and 24 and the first distal end opening 30 of the first catheter 18. The catheter assembly 12 is preferably about 5 to about 10 times the length of the guide tube (not shown).

FIG. 3 is an enlarged lengthwise, sectional perspective view of the coterminous body end openings 14 and 20 of the first and second catheters 18 and 24 shown in FIG. 2 received in the rounded forward end opening 27 of the guide tube 26. The diameter of the guide tube 26 is large enough to permit passage of the catheter assembly therethrough, with substantially no friction therebetween. Preferably, the coterminous body end openings 14 and 20 of the first and second catheters 18 and 24 are rounded to minimize adhering to tissue and to facilitate maneuverability within the uterus.

FIG. 4 is an enlarged cross-sectional view of the coterminous body end openings 14 and 20 of the first and second catheters 18 and 24, taken substantially along the line 4—4 of FIG. 3. As can be seen in FIG. 4, the respective lumens 16 and 22 of the first and second catheters 18 and 24 are substantially circular in circumference, and the guide tube 26 is configured in a substantially circular circumference for receiving the catheter assembly 12. In the embodiment illustrated in FIG. 4, the first and second catheters 18 and 24 define lumens 16 and 22 of equal internal cross-sectional diameter. A particularly preferred internal diameter is about 2 millimeters. In the embodiment shown in FIG. 4, the lumens 16 and 22 are bonded at their contiguous portion 28 in the manner described previously.

FIG. 5 is an enlarged cross-sectional view similar to FIG. 4, but illustrating a further embodiment of the respective body end openings 14 and 20 of the catheter assembly 12 where the respective lumens 16 and 22 of the first and second catheters 18 and 24 are divided from each other by a common internal wall 70 along the contiguous parallel portions of their respective paths. In this embodiment, the paths of the respective lumens 16 and 22 of the first and second catheters 18 and 24 are separable beyond the contiguous portion by a separating juncture (not shown) located as shown in FIG. 2 at 52. The respective lumens 16 and 22 as shown are substantially semicircular, but can be circular in circumference. A particularly preferred embodiment has an exterior wall 58 and 58' thickness of about 0.4 millimeters and an internal wall 70 thickness of about 0.8 millimeters along the contiguous portion.

It will be appreciated that the overall external circumferential diameter of the catheter assembly should be the smallest possible capable of practicing the principles of this invention so as to minimize interference with delivery of the fetus and to minimize the chance of perforating the uterus. A particularly desirable useful circumferential dimension for the catheter assembly is about 5.6 millimeters by 2.8 millimeters and for the guide tube of about 8 millimeters by 5 millimeters. A useful wall thickness for the first and second catheters is about 0.4 millimeters, and a useful wall thickness for the guide tube is about 1 millimeter. A useful internal dimension for the guide tube is about 6 millimeters by 3 millimeters, and a useful path length for the guide tube is about 20 to about 26 centimeters. Preferably, the guide tube is arcuate in configuration at its forward end opening portion.

The apparatus of this invention is preferably made of disposable, flexible, substantially translucent polymeric material. It will be appreciated that the materials used in manufacturing the apparatus of this invention and fitments operatively associated therewith are non-toxic and physiologically compatible with body fluids and tissues, such as polypropylene or polyethylene, and are packaged in sterile condition for a one-time use.

While the respective body end openings of the first and second catheters are illustrated as being substantially coterminous, it is recognized that they could be in stepped relationship to each other. However, a stepped relationship is not a preferred embodiment because it increases the risk of perforating the uterus and causing infection.

The apparatus of this invention has certain conventional fitments, the details of which, though not fully illustrated or described, will be apparent to those having skill in the art and an understanding of the necessary function of such fitments.

Briefly described, a method aspect for practicing amnioinfusion therapy with an apparatus of this invention comprises the steps of
  providing an apparatus of this invention comprised of a catheter assembly and a guide tube as described herein before;
  providing a fluid-filled catheter assembly thereof by flushing the respective first and second catheters of the catheter assembly with a sterile fluid to retain fluid therein;
  receiving the coterminous body end openings of the fluid-filled catheter assembly in the guide tube within the body cavity of the vaginal canal through the cervical canal;
  introducing the fluid-filled catheter assembly into the uterus by advancing the catheter assembly through the forward end opening of the guide tube;
  removing the guide tube;
  separating the second distal end opening of the second catheter from the path of the first distal end opening of the first catheter;
  adapting the first distal end opening of the first catheter in operative association with a transducer;
  adapting the second distal end opening of the second catheter in sterile operative association with an infusion bag containing a sterile infusible fluid; and
  monitoring intrauterine fluid pressure transmitted through the first lumen of the first catheter and delivering the infusible fluid through the second lumen of the second catheter of the catheter assembly.

In practicing the above method, the guide tube can be removed in the removing step by sliding the guide tube rearwardly from the coterminous end openings of the catheter assembly to a point beyond the second distal end opening of the second catheter. Alternatively, the guide tube can be provided with a weakening point along a lateral wall, such as by a scored line. In this instance, the guide tube can be removed in the removing step by sliding it rearwardly from the coterminous body end openings of the catheter assembly to a point beyond the body cavity and then removing the guide tube from the catheter assembly by applying relatively mild pressure at the weakening point.

A particularly preferred method aspect for relieving fetal distress during the intrapartum period of advanced labor with ruptured membranes in a human body comprises the steps of:
  providing an apparatus of this invention comprising
  (1) a flexible catheter assembly comprised of a first catheter and a second catheter with their respective first and second lumens parallel and in close proximity to each other along a contiguous portion of about 40 to about 50 percent of their coterminous respective paths rearward of their respective first and second body end opening and first and second distal end opening, the respective distal end openings of the first catheter and second catheter being readily separable in their non-contiguous spaced position, the catheter assembly being further provided with an indicia at a distance of about 18 to about 25 percent of the length of the first catheter rearwardly of its body end opening, and
  (2) a flexible guide tube open at both ends having a rearward end opening for ingress of the catheter assembly and a rounded end opening for egress of the catheter assembly;

providing a fluid-filled catheter assembly thereof by flushing the first catheter with sterile water through its first distal end opening, flushing the second catheter with sterile water through its second distal end opening;

sealing the second distal end opening of the resulting fluid-filled second catheter with a temporary cap to maintain sterility until use;

receiving the coterminous body end openings of the first and second catheters of the fluid-filled catheter assembly in the guide tube intermediate the rearward end opening and the forward end opening of the guide tube;

advancing the fluid-filled catheter assembly and guide tube within the body cavity of the vaginal canal through the cervical canal;

introducing the coterminous body end opening of the first and second catheters of the catheter assembly via the vaginal and cervical canal into the uterus by advancing the catheter assembly through the forward end opening of the guide tube until the egress of the catheter assembly therethrough brings the indicia to the vaginal introitus;

removing the guide tube from the vaginal canal;

sliding the guide tube rearwardly along the catheter assembly to a point beyond the contiguous portion of the catheter assembly;

securing the catheter assembly to a portion of the human body, such as the thigh or abdomen, intermediate the indicia and the guide tube;

sliding the guide tube rearwardly beyond the second distal end opening of the second catheter;

separating the second distal end opening of the second catheter from the path of the first distal end opening of the first catheter;

adapting the first distal end opening of the first catheter for connection in operative association with a transducer and providing a syringe having its leading edge in fluid communication with a first fluid control valve means intermediate the first distal end opening of the first catheter and the transducer;

removing the temporary cap from the distal end opening of the second catheter;

adapting the second distal end opening of the second catheter for connection in operative association with an infusion bag containing an infusible fluid by providing a sterile second fluid control valve intermediate the distal end opening of the second catheter and the infusion bag;

monitoring intrauterine pressure transmitted through the first lumen of the first catheter operatively associated with the transducer; and delivering infusible fluid to the uterus through the second lumen of the second catheter operatively associated with the infusion bag when necessary to replenish the intrauterine fluid.

The practice of the method of this invention can also include the further steps of providing the transducer with a venting control valve means, venting the transducer for a period sufficient to flush the first catheter with a sterile fluid, preferably water, by means of the syringe, to clear the first catheter in the event that the intrauterine fluids accumulate therein during the monitoring step, and resuming monitoring immediately thereafter. Thus, intrauterine pressure can be monitored throughout the labor in a virtually substantially uninterrupted manner.

From the foregoing, it will be observed that numerous modifications and variations can be effected without departing from the true spirit and scope of the concept of the present invention. It is to be understood that no limitation with respect to the specific embodiments disclosed herein is intended or should be inferred. It is, of course, intended to cover, by the appended claims, all such modifications as fall within the scope of the claims.

What is claimed is:

1. An apparatus for simultaneously monitoring intrauterine pressure and delivering infusible fluids therein for purposes of relieving fetal distress in a body during labor with ruptured membranes comprising a flexible catheter assembly comprising a first catheter and a second catheter, said first catheter defining a first lumen being in fluid communication with a first body end opening a first distal end opening, said first body end opening of said first catheter having a plurality of perforations along an external wall of the tip portion of said first body end opening positioned in the uterus, said first distal end opening being adapted for connection to a transducer, said second catheter defining a second lumen being in fluid communication with a second body end opening and a second distal end opening, said distal end opening being adapted for connection to an infusion bag containing an infusible fluid, said first and second catheters being substantially coterminous at their respective body end openings and being in substantially contiguous spaced relationship with their respective lumens parallel and in close proximity to each other along a substantially major portion of their respective paths rearwardly of their respective body end opening and distal end opening, said respective lumens being separable to be non-contiguous in their respective paths beyond said contiguous portion, said first catheter and said second catheter each defining respective lumens of equal internal cross-sectional diameter and each being substantially circular in circumference; and a flexible guide tube open at both ends with a rearward end opening for ingress of said catheter assembly and a rounded forward end opening for egress of said catheter assembly, said guide tube being substantially circular in circumference and arcuate in configuration at its forward end opening to define a path within the vaginal canal and cervical canal of the human body, said guide tube being sized to receive said catheter assembly and permit passage of said catheter assembly therethrough for intrauterine positioning of the coterminous body end openings of the first and second catheters, said guide tube being further configured to slide rearwardly along the path of said catheter assembly when said catheter assembly is so positioned for removal from said vaginal canal, said catheter assembly being substantially longer and more flexible than said guide tube, said guide tube having an inner diameter large enough to permit passage of the said catheter assembly therethrough with substantially no friction therebetween;

so constructed and arranged that said intrauterine pressure is monitored through said first lumen of said first catheter during a period of flux while said fluid is delivered into the uterus through said second lumen of the second catheter when said catheter assembly is positioned in the uterus.

2. The apparatus of claim 1 wherein said catheter assembly is further provided with an indicia intermediate said respective body end openings and distal end openings, said indicia positioned on said substantially contiguous portions of the respective paths of said first catheter and said second catheter and at a point of about 18 to about 25 percent of the length of said first catheter rearwardly of said first body end opening.

3. The apparatus of claim 1 wherein the length of the catheter assembly is stepped at the respective distal end openings of said first catheter and said second catheter, said first distal end opening of said first catheter being substantially longer than said second distal end opening of said second catheter.

4. The apparatus of claim 1 wherein the guide tube is scored along at least one lateral side, said score providing a weakening point for breaking and removing said guide tube from said assembly when said guide tube is removed from said vaginal canal.

5. The apparatus of claim 2 wherein the respective lumens of said first and second catheters are bonded in substantially contiguous spaced relationship along a parallel portion of about 40 to about 50 percent of their respective paths rearwardly of said coterminous body end openings and the second distal end opening of the second catheter, said lumens having a weakening point along said bonding intermediate the indicia and their respective first and second distal end openings, said lumens being separable to be non-contiguous in their respective paths at said weakening point.

6. The apparatus of claim 2 wherein the respective lumens of said first and second catheters are divided from each other by a common internal wall along said contiguous spaced portion of their respective paths, said lumens having a separating juncture beyond said contiguous portion, said lumens being separable to be non-contiguous in their respective paths at said separating point.

7. The apparatus of claim 1 further including a syringe having its leading edge in fluid connection intermediate said transducer and said first distal end opening of said first catheter.

8. The apparatus of claim 1 wherein the catheter assembly is about 5 to about 10 times longer than the guide tube.

9. A flexible catheter assembly for simultaneously monitoring intrauterine pressure and delivering infusible fluids therein comprising a first catheter and a second catherter, said first catheter defining a first lumen being in fluid communication with a first body end opening and a first distal end opening, said first body opening having a plurality of perforations along an external wall portion of the tip, and said first distal end opening being adapted for connection to a transducer, said second catherter defining a second lumen being in fluid communication with a second body end opening and a second distal end opening, said second distal end opening being adapted for connection to an infusion bag containing an infusible fluid, said first and second catheters being substantially coterminous at their respective body end openings, said catheter assembly further provided with an indicia intermediate the respective body end openings and distal end openings, the respective lumens of said first and second catheters being bonded in substantially contiguous spaced relationship along a parallel portion of their respective paths rearwardly of said coterminous body openings and the second distal opening of the second catheter, said lumens having a weaking point along bonding intermediate the indicia and their respective first and second distal end openings, said lumens being separable to be non-contiguous in their respective paths at said weakening point, said catheter assembly being so constructed and arranged that said intrauterine pressure is monitored through said first lumen of said first catheter during a period of flux while said infusible fluid is delivered into the uterus through said second lumen of said second catheter when said catheter assembly is positioned in the uterus.

10. The apparatus of claim 2 made of disposable polymeric material that is substantially translucent and packaged in sterile condition.

* * * * *

UNITED STATES PATENT AND TRADEMARK OFFICE
CERTIFICATE OF CORRECTION

PATENT NO. : 4,722,730

DATED : February 2, 1988

INVENTOR(S) : Jeffrey Levy and Bruce Rosenzweig

It is certified that error appears in the above-identified patent and that said Letters Patent is hereby corrected as shown below:

Column 10, line 17, --and-- should be inserted after the first-mentioned "opening".

Column 10, line 26, --second-- should be inserted before "distal".

Column 10, line 66, --infusible-- should be inserted before "fluid".

Column 12, line 29, --said-- should be inserted before "bonding".

Signed and Sealed this

Twenty-seventh Day of December, 1988

Attest:

DONALD J. QUIGG

Attesting Officer      Commissioner of Patents and Trademarks